US00PP29733P2

(12) United States Plant Patent
Volmary

(10) Patent No.: US PP29,733 P2
(45) Date of Patent: Oct. 9, 2018

(54) ***THUNBERGIA* PLANT NAMED 'VOLTHU 7898'**

(50) Latin Name: *Thunbergia alata*
Varietal Denomination: VOLTHU 7898

(71) Applicant: Hubertus Volmary, Muenster (DE)

(72) Inventor: Hubertus Volmary, Muenster (DE)

( * ) Notice: Subject to any disclaimer, the term of this patent is extended or adjusted under 35 U.S.C. 154(b) by 0 days.

(21) Appl. No.: 15/731,228

(22) Filed: May 5, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Susan Beth McCormick Ewoldt
(74) *Attorney, Agent, or Firm* — C. A. Whealy

(57) ABSTRACT

A new and distinct cultivar of *Thunbergia* plant named 'VOLTHU 7898', characterized by its upright and vining plant habit; freely branching habit; dense and bushy plant form; freely flowering habit; large light red purple-colored flowers; and good garden performance.

2 Drawing Sheets

Botanical designation: *Thunbergia alata.*
Cultivar denomination: 'VOLTHU 7898'.

BACKGROUND OF THE INVENTION

The present invention relates to a new and distinct cultivar of *Thunbergia* plant, botanically known as *Thunbergia alata*, and hereinafter referred to by the name 'VOLTHU 7898'.

The new *Thunbergia* plant is a product of a planned breeding program conducted by the Inventor in Muenster, Germany. The objective of the breeding program is to create new freely-flowering *Thunbergia* plants with unique flower colors and long flowering period.

The new *Thunbergia* plant originated from an open-pollination during the summer of 2013 in Muenster, Germany of an unnamed proprietary selection of *Thunbergia alata*, not patented, as the female, or seed, parent with an unknown selection of *Thunbergia alata* as the male, or pollen, parent. The new *Thunbergia* plant was discovered and selected by the Inventor as a single flowering plant from within the progeny of the stated open-pollination in a controlled environment in Muenster, Germany during the summer of 2014.

Asexual reproduction of the new *Thunbergia* plant by terminal cuttings in a controlled greenhouse environment in Muenster, Germany since the late summer of 2014 has shown that the unique features of this new *Thunbergia* plant are stable and reproduced true to type in successive generations.

SUMMARY OF THE INVENTION

Plants of the new *Thunbergia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'VOLTHU 7898'. These characteristics in combination distinguish 'VOLTHU 7898' as a new and distinct *Thunbergia* plant:

1. Upright and vining plant habit.
2. Freely branching habit; dense and bushy plant form.
3. Freely flowering habit.
4. Large light red purple-colored flowers.
5. Good garden performance.

Plants of the new *Thunbergia* can be compared to plants of the female parent selection. Plants of the new *Thunbergia* differ from plants of the female parent selection primarily in the following characteristics:

1. Plants of the new *Thunbergia* are more freely flowering than plants of the female parent selection.
2. Plants of the new *Thunbergia* and the female parent selection differ in flower color as plants of the female parent selection have lavender purple-colored flowers.
3. Plants of the new *Thunbergia* have better garden performance than plants of the female parent selection.

Plants of the new *Thunbergia* can be compared to plants of *Thunbergia grandiflora* 'Daniella', disclosed in U.S. Plant Pat. No. 12,893. In side-by-side comparisons, plants of the new *Thunbergia* differ from plants of 'Daniella' in the following characteristics:

1. Plants of the new *Thunbergia* are more compact and have shorter internodes than plants of 'Daniella'.
2. Plants of the new *Thunbergia* have smaller and lighter green-colored leaves than plants of 'Daniella'.
3. Plants of the new *Thunbergia* are more freely flowering than plants of 'Daniella'.
4. Plants of the new *Thunbergia* have smaller flowers than plants of 'Daniella'.
5. Plants of the new *Thunbergia* and 'Daniella' differ in flower color as plants of 'Daniella' have lavender (violet blue)-colored flowers.
6. Plants of the new *Thunbergia* have better garden performance than plants of 'Daniella'.

BRIEF DESCRIPTION OF THE PHOTOGRAPHS

The accompanying colored photographs illustrate the overall appearance of the new *Thunbergia* plant showing the colors as true as it is reasonably possible to obtain in colored reproductions of this type. Colors in the photographs may differ slightly from the color values cited in the detailed botanical description which accurately describe the colors of the new *Thunbergia* plant.

The photograph on the first sheet comprises a side perspective view of a typical flowering plant of 'VOLTHU 7898' grown in an outdoor nursery.

The photograph on the second sheet is a close-up view of a typical flowering plant of 'VOLTHU 7898'.

DETAILED BOTANICAL DESCRIPTION

The aforementioned photographs and following observations, measurements and values describe plants grown during the spring in three-liter containers in an outdoor nursery and a glass-covered greenhouse in Muenster, Germany and under cultural practices typical of commercial *Thunbergia* production. During the production of the plants, day temperatures ranged from 18° C. to 20° C., night temperatures ranged from 15° C. to 18° C. and light levels ranged from 5,000 to 40,000 lux. Plants were pinched one time about three weeks after planting. Plants were 16 weeks old when the photographs and description were taken. In the following description, color references are made to The Royal Horticultural Society Colour Chart, 2015 Edition, except where general terms of ordinary dictionary significance are used.

Botanical classification: *Thunbergia alata* 'VOLTHU 7898'.

Parentage:

- *Female, or seed, parent*.—Unnamed proprietary selection of *Thunbergia alata*, not patented.
- *Male or pollen parent*.—Unknown selection of *Thunbergia alata*, not patented.

Propagation:

- *Type*.—By terminal cuttings.
- *Time to initiate roots, summer*.—About one to two weeks at temperatures about 20° C. to 25° C.
- *Time to initiate roots, winter*.—About two to three weeks at temperatures about 15° C. to 23° C.
- *Time to develop roots, summer*.—About three weeks at temperatures about 20° C. to 25° C.
- *Time to develop roots, winter*.—About 30 days at temperatures about 15° C. to 23° C.
- *Root description*.—Fine, fibrous; typically yellowish white in color, actual color of the roots is dependent on substrate composition, water quality, fertilizer type and formulation, substrate temperature and physiological age of roots.
- *Rooting habit*.—Freely branching; medium density.

Plant description:

- *Plant and growth habit*.—Upright and vining plant habit; plants require support; moderately vigorous to vigorous growth habit; moderately rapid growth rate.
- *Branching habit*.—Freely branching habit with lateral branches potentially developing at every node; pinching enhances lateral branch development; bushy and dense habit.
- *Plant height*.—About 80 cm to 100 cm.
- *Plant diameter* (*area of spread*).—About 35 cm.

Lateral branch description:

- *Length*.—About 50 cm.
- *Diameter*.—About 1.5 mm.
- *Internode length*.—About 14.5 cm.
- *Texture*.—Slightly pubescent.
- *Strength*.—Strong, flexible.
- *Color*.—Close to 60A; at the internodes, close to 144B.

Leaf description:

- *Arrangement*.—Opposite, simple.
- *Length*.—About 11.5 cm.
- *Width*.—About 8 cm.
- *Shape*.—Roughly deltoid.
- *Apex*.—Acute to cuspidate.
- *Base*.—Sagittate.
- *Margin*.—Entire.
- *Aspect*.—Horizontal to somewhat downward.
- *Texture and luster, upper and lower surfaces*.—Pubescent; dull.
- *Venation pattern*.—Pinnate.
- *Color*.—Developing and fully expanded leaves, upper surface: Close to 146A; venation, close to 146A. Developing and fully expanded leaves, lower surface: Close to 146B; venation, close to 149D.
- *Petioles*.—Length: About 3 cm. Diameter: About 3 mm. Texture, upper and lower surfaces: Pubescent. Color, upper and lower surfaces: Proximally, close to N79B; distally, close to 143B.

Flower description:

- *Flower type and habit*.—Single axillary salverform flowers; freely flowering habit with numerous flowers developing per plant; flowers face outward to slightly drooping.
- *Natural flowering season*.—Plants flower continuously from April until frost in Germany; plants begin flowering about ten to twelve weeks after planting.
- *Flower longevity*.—Flowers last about five days on the plant; flowers persistent.
- *Fragrance*.—None detected.
- *Flower diameter*.—About 5.5 cm to 6.3 cm.
- *Flower length* (*height*).—About 5.5 cm to 6.3 cm.
- *Flower buds*.—Length: About 2.2 cm. Diameter: About 1.8 cm. Shape: Lanceolate to deltoid. Color: Close to 144B.
- *Petals*.—Arrangement: Corolla consists of five petals in a single whorl and fused towards the base. Length: About 2.6 cm. Width: About 2 cm. Shape: Broadly elliptic to rounded. Apex: Broadly emarginate. Base: Fused. Margin: Entire, occasionally incised. Texture and luster, upper and lower surfaces: Smooth, glabrous; matte. Color: When opening, upper surface: Close to 59D; throat, close to N77A. When opening, lower surface: Close to 76C; tube, close to 69C. Fully opened, upper surface: Close to 60A and 60C; venation, close to 58A; throat, close to NN77A; color becoming closer to 75B and venation, close to 73B, with development. Fully opened, lower surface: Close to 76C and 76D; tube, close to N77A.
- *Flower bracts*.—Quantity and arrangement: Two, opposite. Length: About 3 cm. Width: About 2.7 cm. Shape: Spear-shaped. Apex: Obtuse. Base: Cordate. Margin: Entire. Texture and luster, upper and lower surfaces: Slightly pubescent; matte. Color, upper and lower surfaces: Close to 143B.
- *Sepals*.—Sepal development has not been observed on plants of the new *Thunbergia*.
- *Peduncles*.—Length: About 5.4 cm. Diameter: About 1 mm. Angle: About 15° from stem axis. Strength: Strong, flexible. Texture: Densely pubescent. Color: Close to 144B.
- *Reproductive organs*.—Androecium: Stamen number: About four. Filament length: About 5 mm. Filament color: Close to 11D. Anther length: About 1 cm.

Anther shape: Ovate. Anther color: Close to 155D. Amount of pollen: None observed. Gynoecium: Pistil number: One. Style length: About 1.7 cm. Style color: Close to NN155D. Stigma appearance: Biparted. Stigma color: Close to NN155D. Ovary color: Close to NN155D.

*Seeds and fruits*.—Seed and fruit development has not been observed on plants of the new *Thunbergia* to date.

Garden performance: Plants of the new *Thunbergia* have been observed to have good garden performance and to tolerate rain, wind and temperatures ranging from about 5° to about 38° C.

Pathogen & pest resistance: Plants of the new *Thunbergia* have not been shown to be resistant to pathogens and pests common to *Thunbergia* plants.

It is claimed:

1. A new and distinct *Thunbergia* plant named 'VOLTHU 7898' as illustrated and described.

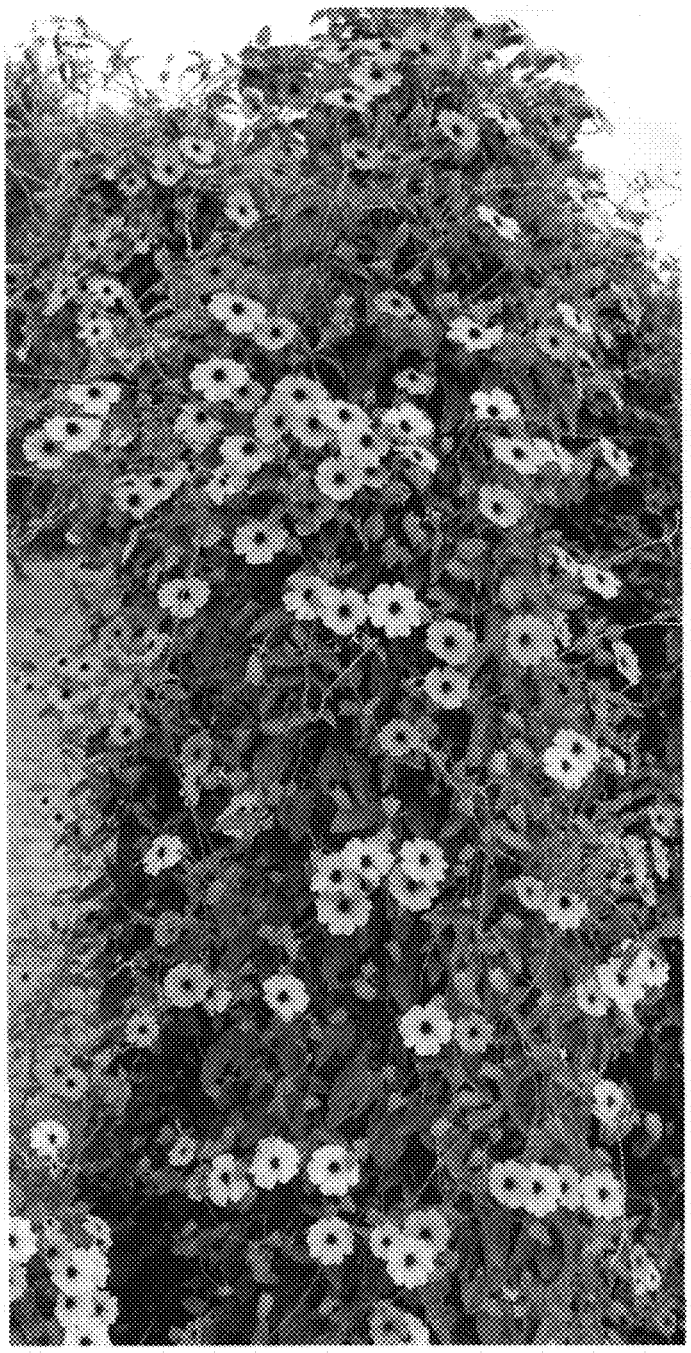

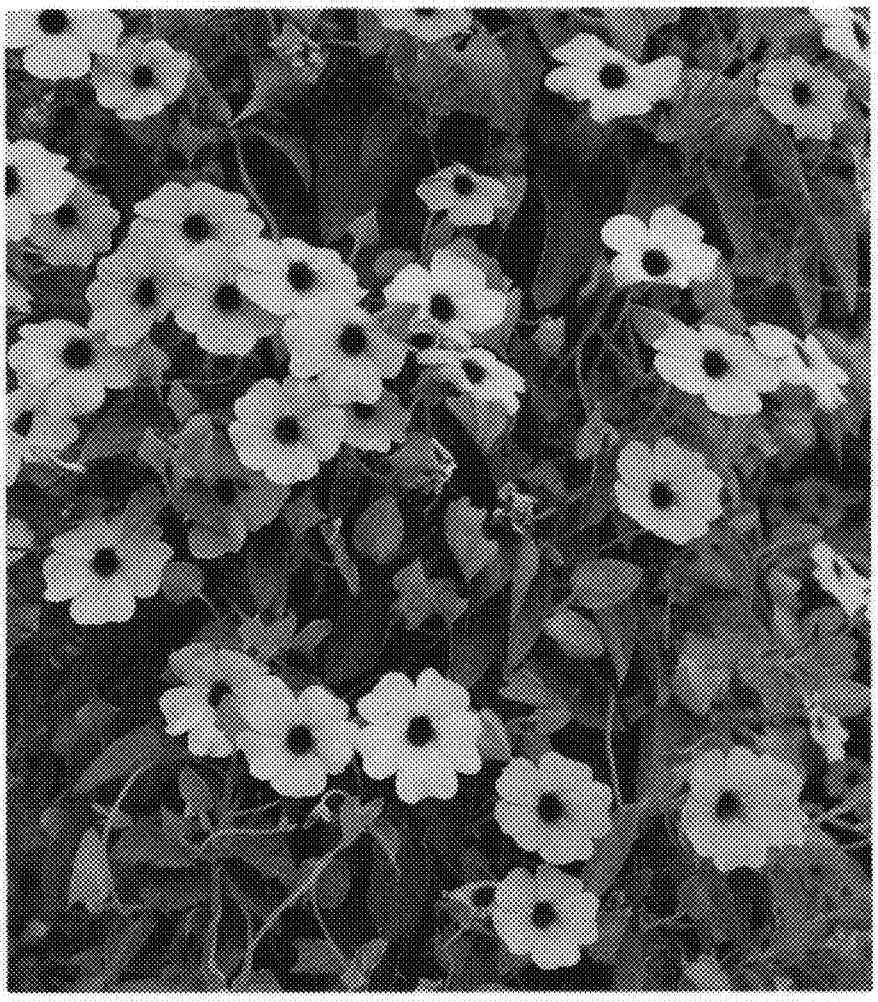

* * * * *